US012588859B2

(12) United States Patent
Yeung

(10) Patent No.: US 12,588,859 B2
(45) Date of Patent: Mar. 31, 2026

(54) SYSTEM AND METHOD FOR INTERACTING WITH HUMAN BRAIN ACTIVITIES USING EEG-fNIRS NEUROFEEDBACK

(71) Applicant: The Education University of Hong Kong, Hong Kong (HK)

(72) Inventor: Kin Chung Michael Yeung, Hong Kong (HK)

(73) Assignee: The Education University of Hong Kong, Hong Kong (HK)

( * ) Notice: Subject to any disclaimer, the term of this patent is extended or adjusted under 35 U.S.C. 154(b) by 0 days.

(21) Appl. No.: 18/613,064

(22) Filed: Mar. 21, 2024

(65) Prior Publication Data

US 2025/0295350 A1      Sep. 25, 2025

(51) Int. Cl.
*A61B 5/369* (2021.01)
*A61B 5/00* (2006.01)
(Continued)

(52) U.S. Cl.
CPC ............ *A61B 5/369* (2021.01); *A61B 5/0075* (2013.01); *A61B 5/375* (2021.01); *A61B 5/7282* (2013.01);
(Continued)

(58) Field of Classification Search
CPC ....... A61B 5/369; A61B 5/0075; A61B 5/375; A61B 5/7282; A61B 5/743; A61B 5/165;
(Continued)

(56) References Cited

U.S. PATENT DOCUMENTS

2004/0073129 A1* 4/2004 Caldwell ................ A61B 5/291
600/544
2007/0282566 A1* 12/2007 Whitlow ................ G06Q 10/06
702/182
(Continued)

OTHER PUBLICATIONS

Amal Alabdulkareem et al., "A Systematic Review of Research on Robot-Assisted Therapy for Children with Autism", Sensors, 2022, vol. 22, No. 944, p. 1-16.
(Continued)

*Primary Examiner* — Jack Yip
(74) *Attorney, Agent, or Firm* — Idea Intellectual Limited; Sam T. Yip

(57) ABSTRACT

An integrated EEG-fNIRS neurofeedback system for interacting with participant's brain activity includes EEG electrodes, fNIRS detectors, at least one information receiver, a computation module, and a report generator. The EEG electrodes collect EEG signals. The fNIRS detectors collect fNIRS signals. The at least one information receiver receives and processes the collected EEG and fNIRS signals. The computation module executes an EEG and fNIRS signal processing pipeline with the EEG electrodes, the fNIRS detectors, and the information receiver. The computation module is further configured to: calculate score information based on received EEG and fNIRS signals; select a minimum score from the calculated score information; and discard an alternative score that is not selected as the minimum score, so as to enable the computation module to choose a single representative score for the shared target objective from both EEG and fNIRS signals. The report generator provides a report of the selection.

12 Claims, 6 Drawing Sheets

(51) Int. Cl.
| | |
|---|---|
| *A61B 5/375* | (2021.01) |
| *A61B 5/16* | (2006.01) |
| *A61B 5/291* | (2021.01) |
| *A61B 5/377* | (2021.01) |
| *G06F 3/01* | (2006.01) |

(52) U.S. Cl.
CPC .............. *A61B 5/743* (2013.01); *A61B 5/165* (2013.01); *A61B 5/291* (2021.01); *A61B 5/377* (2021.01); *A61B 5/6803* (2013.01); *G06F 3/015* (2013.01)

(58) Field of Classification Search
CPC ....... A61B 5/291; A61B 5/377; A61B 5/6803; G06F 3/015
See application file for complete search history.

(56) References Cited

U.S. PATENT DOCUMENTS

| | | | | |
|---|---|---|---|---|
| 2011/0054342 A1* | 3/2011 | Matthews, Jr. | ........ | A61B 5/369 |
| | | | | 600/545 |
| 2012/0051588 A1* | 3/2012 | McEldowney | ........ | G03B 21/14 |
| | | | | 348/46 |
| 2012/0296569 A1* | 11/2012 | Shahaf | ................... | A61B 5/383 |
| | | | | 702/19 |
| 2015/0313496 A1* | 11/2015 | Connor | ................ | A61B 5/6814 |
| | | | | 600/301 |
| 2018/0368719 A1* | 12/2018 | Prat | ........................ | A61B 5/375 |
| 2021/0282718 A1* | 9/2021 | Barthelemy | ......... | A61B 5/7221 |
| 2024/0307246 A1* | 9/2024 | Harch | ................... | A61M 21/00 |
| 2024/0366157 A1* | 11/2024 | Moses | ...................... | A61B 5/24 |
| 2025/0025660 A1* | 1/2025 | Faghih | ................... | G16H 50/30 |

OTHER PUBLICATIONS

Martijn Arns et al., "Efficacy of neurofeedback treatment in ADHD: the effects on inattention, impulsivity and hyperactivity: a meta-analysis", Clinical EEG and Neuroscience, 2009, vol. 40, No. 3, p. 180-189.

Martijn Arns et al., "Evaluation of neurofeedback in ADHD: the long and winding road", Biological Psychology, 2014, vol. 95, p. 108-115.

Ru Ying Cai et al., "Emotion regulation in autism spectrum disorder: Where we are and where we need to go", Autism Research, 2018, vol. 11, p. 962-978.

Bruce F. Chorpita et al., "Assessment of symptoms of DSM-IV anxiety and depression in children: A revised child anxiety and depression scale", Behaviour Research and Therapy, 2000, vol. 38, p. 835-855.

John T. Danial et al., "Cognitive behavioral therapy for children with autism: review and considerations for future research", Journal of Developmental & Behavioral Pediatrics, 2013, vol. 34, No. 9, p. 702-715.

D. T. Delpy et al., "Estimation of optical pathlength through tissue from direct time of flight measurement", Physics in Medicine & Biology, 1988, vol. 33, No. 12, p. 1433-1442.

EA Demetriou et al., "Autism spectrum disorders: a meta-analysis of executive function", Molecular Psychiatry, 2018, vol. 23, p. 1198-1204.

Ann-Christine Ehlis et al., "Near-infrared spectroscopy as a new tool for neurofeedback training: Applications in psychiatry and methodological considerations", Japanese Psychological Research, 2018, vol. 60, No. 4, p. 225-241.

Stefanie Enriquez-Geppert et al., "EEG-neurofeedback as a tool to modulate cognition and behavior: a review tutorial", Frontiers in Human Neuroscience, 2017, vol. 11, No. 51, p. 1-19.

J. Fernández-Alvarez et al., "Efficacy of bio-and neurofeedback for depression: a meta-analysis", Psychological Medicine, 2022, vol. 52, p. 201-216.

Elisabeth V. C. Friedrich et al., "An effective neurofeedback intervention to improve social interactions in children with autism spectrum disorder", Journal of Autism and Developmental Disorders, 2015, vol. 45, p. 4084-4100.

Holger Gevensleben et al., "Neurofeedback training in children with ADHD: 6-month follow-up of a randomised controlled trial", European Child & Adolescent Psychiatry, 2010, vol. 19, p. 715-724.

Ayegül Güven et al., Combining functional near-infrared spectroscopy and EEG measurements for the diagnosis of attention-deficit hyperactivity disorder, Neural Computing and Applications, 2020, vol. 32, p. 8367-8380.

D. Corydon Hammod, "Neurofeedback with anxiety and affective disorders", Child and Adolescent Psychiatric Clinics, 2005, vol. 14, p. 105-123.

Patricia Howlin et al., "Adults with autism spectrum disorders", The Canadian Journal of Psychiatry, 2012, vol. 57, No. 5, p. 275-283.

Ryan O. Kellems et al., "Social Engagement of Elementary-Aged Children With Autism Live Animation Avatar Versus Human Interaction", Journal of Special Education Technology, 2022, vol. 38, p. 327-339.

Ann-Christin S. Kimmig et al., "Feasibility of NIRS-based neurofeedback training in social anxiety disorder: behavioral and neural correlates", Journal of Neural Transmission, 2019, vol. 126, p. 1175-1185.

Irving Kirsch et al., "Initial severity and antidepressant benefits: a meta-analysis of data submitted to the Food and Drug Administration", PLoS Medicine, 2008, vol. 5, No. e45, p. 0260-0268.

Silvia Erika Kober et al., Age-related differences in the within-session trainability of hemodynamic parameters: a near-infrared spectroscopy-based neurofeedback study, Neurobiology of Aging, 2019, vol. 81, p. 127-137.

Simon H. Kohl et al., "The Potential of Functional Near-Infrared Spectroscopy-Based Neurofeedback—A Systematic Review and Recommendations for Best Practice", Frontiers in Neuroscience, 2020, vol. 14, No. 594, p. 1-31.

Mirjam E.J. Kouijzer et al., "Neurofeedback improves executive functioning in children with autism spectrum disorders", Research in Autism Spectrum Disorders, 2009, vol. 3, p. 145-162.

Keshuang Li et al., "Functional near-infrared spectroscopy-informed neurofeedback: regional-specific modulation of lateral orbitofrontal activation and cognitive flexibility", Neurophotonics, 2019, vol. 6, No. 025011, p. 1-11.

Ziming Liu et al., "A systematic review on hybrid EEG/fNIRS in brain-computer interface", Biomedical Signal Processing and Control, 2021, vol. 68, No. 102595, p. 1-8.

Antolin M. Llorente et al., "Children's Color Trails Test 1 & 2: test-retest reliability and factorial validity", The Clinical Neuropsychologist, 2009, vol. 23, p. 645-660.

S. Lloyd-Fox et al., "Illuminating the developing brain: the past, present and future of functional near infrared spectroscopy", Neuroscience & Biobehavioral Reviews, 2010, vol. 34, p. 269-284.

Anna-Maria Marx et al., "Near-infrared spectroscopy (NIRS) neurofeedback as a treatment for children with attention deficit hyperactivity disorder (ADHD)—a pilot study", Frontiers in Human Neuroscience, 2015, vol. 8, No. 1038, p. 1-13.

Hengameh Marzibani et al., "Neurofeedback: a comprehensive review on system design, methodology and clinical applications", Basic and Clinical Neuroscience, 2016, vol. 7, No. 2, p. 143-158.

David M. A. Mehler et al., "Targeting the affective brain—a randomized controlled trial of real-time fMRI neurofeedback in patients with depression", Neuropsychopharmacology, 2018, vol. 43, p. 2578-2585.

Nancy J. Minshew et al., "The nature of brain dysfunction in autism: functional brain imaging studies", Current Opinion in Neurology, 2010, vol. 23, p. 124-130.

Celal Perihan et al., "Effects of cognitive behavioral therapy for reducing anxiety in children with high functioning ASD: a systematic review and meta-analysis", Journal of Autism and Developmental Disorders, 2020, vol. 50, p. 1958-1972.

J.A. Pineda et al., "Positive behavioral and electrophysiological changes following neurofeedback training in children with autism", Research in Autism Spectrum Disorders, 2008, vol. 2, p. 557-581.

(56) References Cited

OTHER PUBLICATIONS

Jaime A. Pineda et al., "Neurofeedback training produces normalization in behavioural and electrophysiological measures of high-functioning autism", Philosophical Transactions of the Royal Society B: Biological Sciences, 2014, vol. 369, No. 20130183, p. 1-10.

Clare Reynell et al., "The BOLD signal and neurovascular coupling in autism", Developmental Cognitive Neuroscience, 2013, vol. 6, p. 72-79.

Stella Rosson et al., "Brain stimulation and other biological non-pharmacological interventions in mental disorders: an umbrella review", Neuroscience & Biobehavioral Reviews, 2022, vol. 139, No. 104743, p. 1-18.

G. Michael Russo et al., "A meta-analysis of neurofeedback for treating anxiety-spectrum disorders", Journal of Counseling & Development, 2022, vol. 100, p. 236-251.

Joni N. Saby et al., "The utility of EEG band power analysis in the study of infancy and early childhood", Developmental Neuropsychology, 2012, vol. 37, p. 253-273.

Rebecca C. Shaffer et al., "Brief report: diminished gaze preference for dynamic social interaction scenes in youth with autism spectrum disorders", Journal of Autism and Developmental Disorders, 2017, vol. 47, p. 506-513.

Deborah R. Simkin et al., "Quantitative EEG and neurofeedback in children and adolescents: anxiety disorders, depressive disorders, comorbid addiction and attention-deficit/hyperactivity disorder, and brain injury", Child and Adolescent Psychiatric Clinics, 2014, vol. 23, p. 427-464.

Ranganatha Sitaram et al., "Closed-loop brain training: the science of neurofeedback", Nature Reviews Neuroscience, 2017, vol. 18, p. 86-100.

Steinn Steingrimsson et al., "Electroencephalography-based neurofeedback as treatment for post-traumatic stress disorder: A systematic review and meta-analysis", European Psychiatry, 2020, vol. 63, No. e7, p. 1-12.

"EDB to enhance support for students with autism spectrum disorders", The Government of the Hong Kong Special Administrative Region, 2019 URL: https://www.info.gov.hk/gia/general/201910/03/P2019100300291.htm.

Lucas R. Trambaiolli et al., "Neurofeedback training in major depressive disorder: a systematic review of clinical efficacy, study quality and reporting practices", Neuroscience & Biobehavioral Reviews, 2021, vol. 125, p. 33-56.

Jessica Van Doren et al., "Sustained effects of neurofeedback in ADHD: a systematic review and meta-analysis", European Child & Adolescent Psychiatry, 2019, vol. 28, p. 293-305.

San-Yu Wang et al., "The effects of alpha asymmetry and high-beta down-training neurofeedback for patients with the major depressive disorder and anxiety symptoms", Journal of Affective Disorders, 2019, vol. 257, p. 287-296.

Michael K. Yeung et al., "Altered right frontal cortical connectivity during facial emotion recognition in children with autism spectrum disorders", Research in Autism Spectrum Disorders, 2014, vol. 8, p. 1567-1577.

Michael K. Yeung et al., "Abnormal frontal theta oscillations underlie the cognitive flexibility deficits in children with high-functioning autism spectrum disorders", Neuropsychology, 2016, vol. 30, No. 3, p. 281-295.

Michael K. Yeung et al., "Frontal lobe dysfunction underlies the differential word retrieval impairment in adolescents with high-functioning autism", Autism Research, 2019, vol. 12, p. 600-613.

Michael K. Yeung et al., "Depressive and anxiety symptoms are related to decreased lateral prefrontal cortex functioning during cognitive control in older people", Biological Psychology, 2021, vol. 166, No. 108224, p. 1-10.

Michael K. Yeung et al., "Negative mood is associated with decreased prefrontal cortex functioning during working memory in young adults", Psychophysiology, 2021, vol. 58, No. e13802, p. 1-17.

* cited by examiner

| | Cognitive | Affective | Social |
|---|---|---|---|
| Expected outcome | Enhanced attention and executive function | Reduced mood and anxiety symptoms | Improved social and behavioral symptoms |
| EEG index (electrical) | Frontal theta/beta ratio ↓ | Leftward asymmetry of frontal alpha ↑ | Mu rhythm (a proxy for mirror neuron system activity) ↓ |
| EEG site | Fz | F3, F4 | C3, C4 |
| fNIRS index (hemodynamic) | Frontal activity ↑ | Leftward asymmetry of frontal activity ↑ | Sensorimotor activity ↑ |
| fNIRS site | All frontal channels | All frontal channels | All frontocentral channels |
| Training and feedback stimuli | Play a video of interest to the autistic child (e.g., animated geometric shapes) | Change an avatar or human face from neutral to happy | Watch a video of finger and hand movements |
| Feedback | Playback speed | Happiness level | Horizontal distance from the center screen |
| Training schedule | (Across modules) Customized (default: alternating between 5 minutes of training and 1 minute of rest, for two rounds) | | |
| Difficulty level (Z-score) | (Across modules) Level 1: 0 to 0.5; Level 2: 0 to 1.0; Level 3: 0 to 1.5 | | |
| Reward delivery | (Across modules) One point for every 10% of the Z-score range, updated every second | | |
| Progressive overload | (Across modules) Proceed to the next difficulty level when securing more than 2000 points for two rounds in a row, but revert to the previous level when obtaining fewer than 1,000 points in two consecutive rounds | | |

*Note.* EEG = electroencephalography; fNIRS = functional near-infrared spectroscopy. Z-score represents the number of standard deviations different from baseline.

FIG. 4

Neurofeedback application (EEG = electroencephalography; fNIRS = functional near-infrared spectroscopy)

| | The provided system | Emotiv Pro | BrainMaster Avatar | Thought Technology Biograph Infiniti | Neurosky MindWave | Existing fNIRS software |
|---|---|---|---|---|---|---|
| EEG | | | | | | |
| Neurofeedback | Yes | Yes | Yes | Yes | Yes | No |
| Training protocols targeted for autism | Yes | No | Unclear | Unclear | No | NA |
| Training index | Power and power asymmetry | Power | Power | Power and power asymmetry | Power | NA |
| Efficacy-optimizing features | Use of motivational stimuli, reward delivery, and progressive overload | Reward delivery | Use of motivational stimuli and reward delivery | Use of motivational stimuli and reward delivery | Use of motivational stimuli and reward delivery | NA |
| Artifact control procedure | Filter, blink and eye movement artifact rejection, referencing to the average of mastoids (to avoid biases towards one side), and shielding from powerline noise | Filtering | Filtering and referencing to the average of mastoids (to avoid biases towards one side) | Filtering | Filtering | NA |
| Compatibility with fNIRS and third-party systems | Yes | No | No | No | No | NA |
| fNIRS | | | | | | |
| Neurofeedback | Yes | NA | NA | NA | NA | No |
| Training protocols targeted for autism | Yes | NA | NA | NA | NA | NA |
| Training index | Amplitude and amplitude asymmetry | NA | NA | NA | NA | NA |
| Efficacy-optimizing features | Use of motivational stimuli, reward delivery, and progressive overload | NA | NA | NA | NA | NA |
| Artifact control procedure | Short-separation channel subtraction (to remove extracerebral blood flow confounds) | NA | NA | NA | NA | NA |
| Compatibility with EEG and third-party systems | Yes | NA | NA | NA | NA | NA |

FIG. 6

SYSTEM AND METHOD FOR INTERACTING WITH HUMAN BRAIN ACTIVITIES USING EEG-fNIRS NEUROFEEDBACK

FIELD OF THE INVENTION

The present invention generally relates to techniques of interacting with human brain activities and measuring one's attention level. More specifically the present invention relates to systems and methods using integrated electroencephalography (EEG) and functional near-infrared spectroscopy (fNIRS) neurofeedback in interacting with human brain activities.

BACKGROUND OF THE INVENTION

Autism spectrum disorder (referred to as autism thereafter) is a lifelong neurodevelopmental disability associated with social communication impairment. It is often accompanied by cognitive and emotion regulation difficulties. Autism is increasingly prevalent and diagnosed. Altered brain function is prominent in autism and is associated with cognitive, emotional, and social differences in autistic children. Unfortunately, the brain health of autistic individuals has been relatively neglected. There is also a lack of approaches and technologies available to directly intervene with brain function across sectors. Because many autistic children have poor vocational and health outcomes in adulthood, there is a strong need to develop effective and easy-to-apply neuroscience-based treatments for these children.

In this regard, neurofeedback training using either electroencephalography (EEG) or functional near-infrared spectroscopy (fNIRS) has been shown to bring promising cognitive, emotional, and behavioral benefits to some neuropsychiatric disorders, including autism. Importantly, these technologies are relatively low-cost and user-friendly, making them ideal for remediating brain dysfunction. However, because EEG and fNIRS capture different aspects of brain activity, how to integrate them for arguably augmenting the therapeutic effects of neurofeedback training becomes an issue. Therefore, there is a need for making innovations in developing a versatile combined EEG-fNIRS neurofeedback application to offer synergistic brain training for autistic children.

SUMMARY OF THE INVENTION

It is an objective of the present invention to provide a system and a method to address the aforementioned shortcomings and unmet needs in the state of the art.

In accordance with a first aspect of the present invention, an integrated electroencephalogram-functional near-infrared spectroscopy (EEG-fNIRS) neurofeedback system for interacting with participant's brain activity is provided, including EEG electrodes, fNIRS detectors, an information receiver, a computation module, and a report generator. The EEG electrodes are configured to collect EEG signals. The fNIRS detectors are configured to collect fNIRS signals. The information receiver is electrically coupled with the EEG electrodes and the fNIRS detectors and is configured to receive and process the collected EEG and fNIRS signals from the EEG electrodes and the fNIRS detectors, respectively. The computation module is electrically coupled with the information receiver and is configured to execute an EEG and fNIRS signal processing pipeline with the EEG electrodes, the fNIRS detectors, and the information receiver. The computation module is further configured to: calculate score information based on received EEG and fNIRS signals; select a minimum score from the calculated score information for serving as a common target objective shared by both EEG and fNIRS signals; and discard an alternative score that is not selected as the minimum score, so as to enable the computation module to choose a single representative score for the shared target objective from both EEG and fNIRS signals. The report generator is electrically coupled with the computation module and is configured to provide a report of the selection to the minimum score.

In accordance with a second aspect of the present invention, an integrated EEG-fNIRS neurofeedback method for interacting with participant's brain activity is provided, including steps as follows: collecting EEG signals by EEG electrodes; collecting fNIRS signals by fNIRS detectors; receiving and processing, by a information receiver, the collected EEG and fNIRS signals from the EEG electrodes and the fNIRS detectors, respectively; executing an EEG and fNIRS signal processing pipeline by using the EEG electrodes, the fNIRS detectors, the information receiver, and a computation module; calculating score information based on received EEG and fNIRS signals by the computation module; selecting, by the computation module, a minimum score from the calculated score information for serving as a common target objective shared by both EEG and fNIRS signals; discarding, by the computation module, an alternative score that is not selected as the minimum score, so as to choose a single representative score for the shared target objective from both EEG and fNIRS signals; and providing a report of the selection to the minimum score by a report generator.

Embodiments of the present invention provide a neuroscientific system to realize a novel closed-loop brain training method, called combined electroencephalography (EEG) and functional near-infrared spectroscopy (fNIRS) neurofeedback training. Neurofeedback training teaches participants to self-regulate their own brain activity by providing real-time feedback. One goal is to improve the deviated brain activity and remediate cognitive, emotional, and behavioral problems through brain changes.

In the present disclosure, it aims to develop a versatile EEG-fNIRS neurofeedback system that can be used to enhance cognitive, emotional, and social functioning synergistically for autistic children who need rehabilitation. The key of the present invention is to combine/integrate EEG and fNIRS for neurofeedback training. The metabolic activity of brain cells is supported by increased blood supply, therefore efficient neurovascular coupling is essential for optimal brain functioning. EEG and fNIRS capture two dissociable phenomena in the brain—the electrical field generated by brain cells and hemodynamic activity elicited by neural and/or vascular events. Hence, a combined setup can be expected to augment the therapeutic benefits of neurofeedback training synergistically by facilitating neurovascular coupling. In combined neurofeedback training, the target objective is the conjunction between the EEG and fNIRS indices. For example, if the EEG index is +1 unit, and the fNIRS index is +0.5 unit, the net result will be +0.5 unit.

The neurofeedback system of the present invention further offers at least three training modules proven to be effective in remediating cognitive deficits, emotion dysregulation, and social dysfunction in neuropsychiatric disorders, including autism. (1) For the cognitive module, EEG and fNIRS neurofeedback training requires the downregulation of frontocentral theta/beta ratio (i.e., 4-8 Hz/13-30 Hz power) and frontal cerebral oxygenation (i.e., difference in oxy- and deoxy-hemoglobin concentration), respectively. (2) For the affective module, EEG and fNIRS neurofeedback training involve enhancing the leftward asymmetry of frontal alpha power and frontal cerebral oxygenation, respectively. (3) For the social module, EEG and fNIRS neurofeedback training consist of suppressing the mu rhythm (a proxy for mirror neuron system activation that underlies social cognition) and increasing hemodynamic activity in sensorimotor regions, respectively. For all training modules, combined EEG-fNIRS neurofeedback training can integrate these two indices to encourage self-regulation of neurovascular coupling, or synchronous increases in the brain's electrical and hemodynamic activity.

The EEG-fNIRS neurofeedback system can further utilize ecologically valid feedback stimuli, reward delivery, and progressive overload. These are elements essential for cognitive brain training but are rarely featured in existing neurofeedback products. Reward drives motivation and plays a pivotal role in treatment adherence and efficacy. Traditionally, feedback in neurofeedback training is presented in the form of bar indicators, color patches, or tones, and individuals are simply asked to change these neutral stimuli via implicit self-regulation of their brain activity. In the system of the present disclosure, intrinsically rewarding feedback protocols (e.g., playing a rewarding video and seeing a happy face) are used to maximize motivation. Reward-based personalized training are also implemented, with individuals gaining points in proportion to how closely the target objective is met. Also, depending on performance, the difficulty level (i.e., the extent or rate of change in brain activity) is adjusted to place continuous adequate demand as individuals progress over the course of the training.

The EEG-fNIRS neurofeedback system can further serve as a cross-device and offer high-quality training. The EEG-fNIRS neurofeedback system can operate based on the lab streaming layer (LSL), which is a fully open-source software package for simultaneous recording of time series data. Thus, the developed operation of the EEG-fNIRS neurofeedback system will be compatible with tens of EEG and fNIRS devices that support LSL. In addition, the developed operation of the EEG-fNIRS neurofeedback system, along with the adopted hardware, can ensure that high-quality, uncontaminated signals are used for neurofeedback training. Specifically, the EEG system comprises shielded wet electrodes to isolate from powerline noise, and the applied signal processing pipeline leverages electrooculography (EOG) to reject data segments contaminated by blinks and ocular artifacts. Additionally, the fNIRS part adopted in the system has short-separation channels to remove extracerebral changes in oxy- and deoxy-hemoglobin concentration, enabling training to be performed on hemodynamic activity inside the brain rather than outside. Taken together, the provided EEG-fNIRS neurofeedback system enables training to be conducted with minimal contamination and environmental constraints.

BRIEF DESCRIPTION OF THE DRAWINGS

Embodiments of the invention are described in more details hereinafter with reference to the drawings, in which:

FIG. 4 demonstrates a table for training modules offered in an EEG-fNIRS neurofeedback operation according to one embodiment of the present invention;

FIG. 6 demonstrates a table for comparison between the provided neurofeedback training operation according to one embodiment of the present invention and others in the prior art.

DETAILED DESCRIPTION

Figure 1:
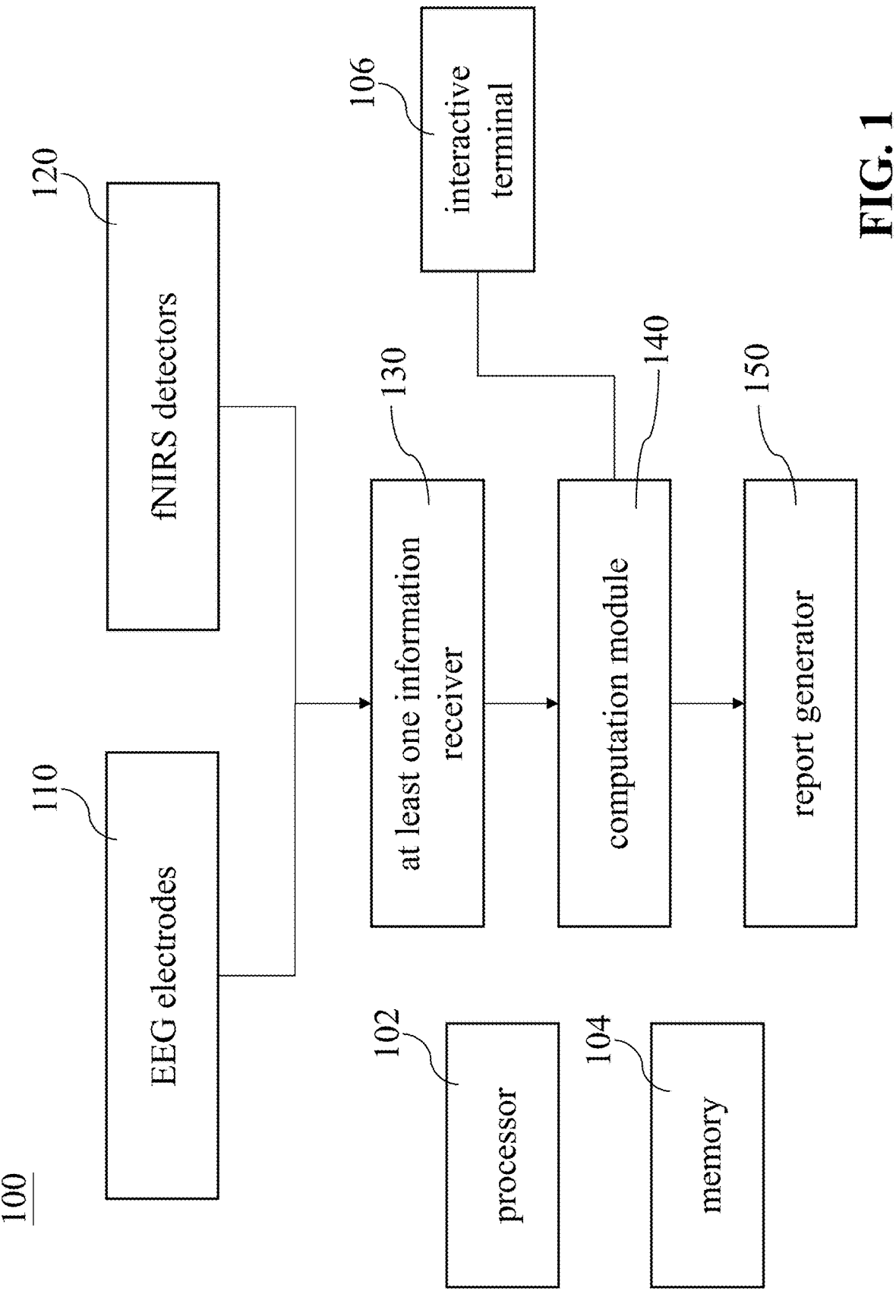
FIG. 1 depicts an architecture of a system using integrated EEG and fNIRS neurofeedback in interacting with a subject's participating activities according to one embodiment of the present invention.

In the following description, systems and methods using integrated electroencephalography (EEG) and functional near-infrared spectroscopy (fNIRS) neurofeedback in interacting with a subject's participating activities and the likes are set forth as preferred examples. It will be apparent to those skilled in the art that modifications, including additions and/or substitutions may be made without departing from the scope and spirit of the invention. Specific details may be omitted so as not to obscure the invention; however, the disclosure is written to enable one skilled in the art to practice the teachings herein without undue experimentation.

For interacting with (or capturing) a subject's participating activities (e.g., human brain activities), the provided system of the present invention can be done using EEG signals, a widely used method to measure brain's electrical activity. Further, the provided system is extended to be conducted using fNIRS signals, an emerging technique that tracks hemodynamic changes in the brain. The neurofeedback training using either EEG or fNIRS has demonstrated promising effects in improving cognitive, emotional, and/or clinical symptoms across mental disorders, including attention deficit/hyperactivity disorder (ADHD), autism, and mood and anxiety disorders. The key feature is how to integrate these two signals.

For EEG, the downregulation of frontocentral theta/beta ratio (4-8 Hz/13-30 Hz) improves attention and executive function in autism and ADHD. The upregulation of frontal alpha asymmetry alleviates negative affective symptoms across mood and anxiety disorders. The suppression of mu rhythm (a proxy for mirror neuron system activation that plays a role in many social cognitive skills) improves everyday socialization and communication skills in autism. For fNIRS, self-regulation of frontal hemodynamic activity has been shown to improve cognition and symptoms in ADHD and anxiety disorders. Thus, neurofeedback training targeting these various indices of brain activity can serve as a direct, comprehensive neurotechnological method for remediating cognitive, emotional, and social dysfunction in autistic children who need habilitation.

The reason for applying the integrated EEG-fNIRS neurofeedback system is provided based on comparative analysis as follows.

Neurofeedback training is a promising alternative treatment approach to autism. Cognitive behavioral therapy is the most popular treatment for autism, and it has been shown to be useful for reducing social communication difficulties and co-occurring emotional and behavioral symptoms in autistic children. However, cognitive behavioral therapies require sufficient cognitive and verbal communication skills and thus are suitable only for high-functioning autistic children. Technological interventions such as those capitalizing on human-robot interactions have also been applied increasingly and shown to be effective in improving social communication skills in autistic children, even for those with limited verbal capabilities. However, evidence about the efficacy of these interventions to improve functioning in non-social domains remains elusive. In comparison, neurofeedback training places relatively little cognitive and verbal demand because individuals are simply asked to obtain reward by interacting with the feedback stimulus. Also, EEG and fNIRS are tolerated well by young individuals, including infants and children. Therefore, EEG-fNIRS neurofeedback training has much potential to offer a versatile solution to enhancing a wide range of functions by intervening with different neural networks.

There are two major categories of noninvasive neurorehabilitation strategies for mental disorders: neurofeedback training and brain stimulation. The former relies on self-regulation of brain activity, whereas the latter leverages external physical influences (e.g., electrical currents or magnetic fields) to alter brain activity or excitability. Both approaches have demonstrated effectiveness in improving cognitive abilities, emotion regulation, and behavioral symptoms across mental disorders. However, unlike brain stimulation, neurofeedback training involves closed-loop neuromodulation, signaling the need for self-regulation based on an individual's brain activity at a given moment (especially when normative data are available). It thus has the advantage of allowing individuals to constantly interact with their own brain activity to achieve an optimal functioning level. Another unique aspect of neurofeedback training is that individuals play the role of active agents in their own training. Through the interplay of self-regulation and reward, their self-efficacy can be increased.

FIG. 1 depicts an architecture of a system 100 using integrated EEG and fNIRS neurofeedback in interacting with a subject's participating activities according to one embodiment of the present invention. The system includes EEG electrodes 110, fNIRS detectors 120, at least one information receiver 130, a computation module 140, and a report generator 150. The system 100 can further include a processor 102 configured to perform operations among these components and a memory 104 configured to store final results (e.g., results from the report generator 150). The system 100 can further include an interactive terminal 106 with a screen which can be configured to display images or videos via the screen, enabling real-time interaction with an intrinsically rewarding stimulus for participants during a game training.

Figure 2:
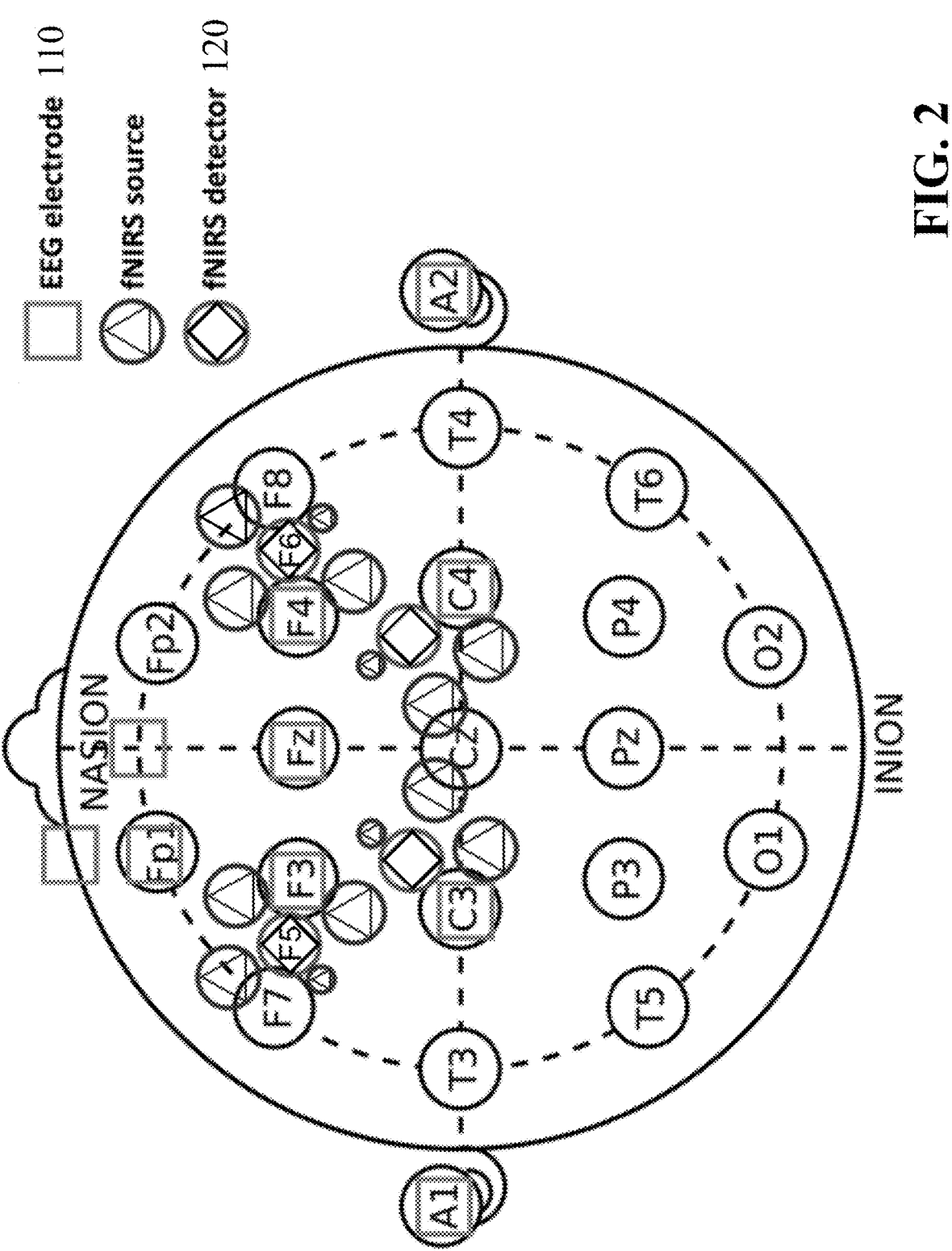
FIG. 2 depicts a schematic layout of EEG electrodes and fNIRS detectors according to one embodiment of the present invention.

FIG. 2 depicts a schematic layout of the EEG electrodes 110 and the fNIRS detectors 120 according to one embodiment of the present invention. The system 100, featuring a combined EEG-fNIRS neurofeedback configuration, integrates EEG electrodes 110 and the fNIRS detectors 120. During neurofeedback sessions, an adjustable recording cap, tailored to the head size, can be utilized to mount both the EEG electrodes 110 and the fNIRS detectors 120. EEG signals captured by the EEG electrodes 110 are recorded by the information receiver 130. The EEG electrodes 110 are placed at regions such as F3, F4, Fz, C3, C4, M1, M2 (reference), and Fpz (ground), as illustrated in FIG. 2. In one embodiment, a vertical electrooculography (EOG) channel is formed using two EEG electrodes 110, with one positioned above the left eye and another below the left eye. The EEG electrodes 110 collect data at a rate of 1,024 Hz. Meanwhile, the fNIRS detectors 120 collect fNIRS signals, which are subsequently transmitted to the information receiver 130 for recording. Two fNIRS detectors 120 are placed on the scalp at the midpoint along regions F3-F7 and regions F4-F8. Each fNIRS detector 120 is surrounded by three fNIRS sources positioned 30 mm apart (long-separation channels) and another fNIRS source positioned 10 mm apart (short-separation channels). Data from the fNIRS detectors 120 is sampled at a rate of 50 Hz.

The at least one information receiver 130 is electrically coupled with the EEG electrodes 110 and the fNIRS detectors 120 and is configured to receive and process the collected EEG and fNIRS signals from the EEG electrodes 110 and the fNIRS detectors 120, respectively, ensuring real-time and accurate extraction of the relevant information. In one embodiment, the information receiver 130 includes an amplifier module for signal processing. The information receiver 130 can package the acquired relevant information and feed them into the computation module 140 for further processing. In one embodiment, the at least one information receiver 130 is established by integrating two or more sub-receiving modules for receiving or extracting the EEG signal and the fNIRS signal, respectively. For example, the information receiver 130 includes one EEG information receiver for the EEG signal specially and one fNIRS information receiver for the fNIRS signal specially, and those receivers cooperate with each other. In one embodiment, the information receiver 130 is a single receiver developed/designed for processing both EEG and fNIRS signals (e.g., dual channel for receiving those different signals).

Figure 3:
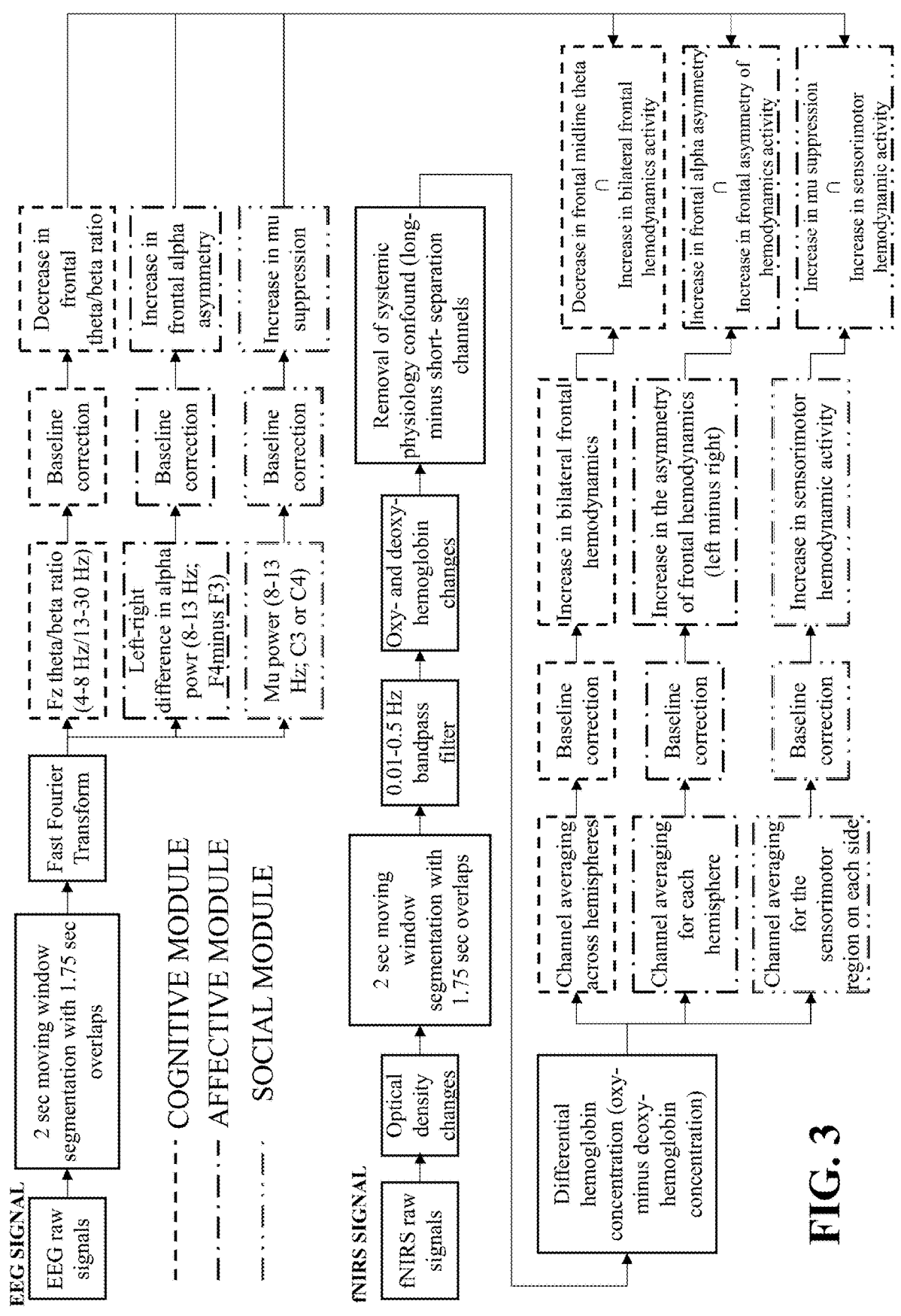
FIG. 3 depicts a processing pipeline for EEG and fNIRS signals according to one embodiment of the present invention.

The computation module 140 electrically coupled with the information receiver 130 and can be configured to execute the EEG and fNIRS signal processing pipeline with the EEG electrodes 110, the fNIRS detectors 120, and the information receiver 130 as shown in FIG. 3.

Details about the EEG and fNIRS signal processing pipeline are shown in FIG. 3. Real-time streaming and integration of EEG and fNIRS signals can be programmed via lab streaming layer (LSL). The provided pipeline can comply with the goal standard for neurofeedback training and can be used flexibly with other EEG and fNIRS systems that support LSL. For both modalities, signals are processed in real time, and features are extracted by the EEG electrodes 110 and the fNIRS detectors 120 with applying a Hamming window function to 2-s moving window epochs (with 1.75-s overlaps). The extracted features can be fed into the computation module 140 via the information receiver 130.

For EEG signals, the target objectives are determined by desired training modules, including a cognitive module, an affective module, and a social module. For the cognitive module, the computation module 140 applies 4-8 Hz and 13-30 Hz bandpass filters to extract EEG power in the theta and beta bands via the corresponding EEG electrodes 110, respectively. The computation module 140 then selects the theta/beta ratio at the Fz region as the target objective. For the affective module, the computation module 140 applies an 8-13 Hz bandpass filter to extract EEG power in the alpha band via the corresponding EEG electrodes 110. The computation module 140 then subtracts the alpha power at the F4 region from that at the F3 region to yield the frontal alpha asymmetry index. For the social module, the computation module 140 applies an 8-13 Hz bandpass filter to extract the mu rhythm via the EEG electrodes 110 at C3 or C4, which can be considered as mirror neuron system activity underlying a wide range of social cognitive skills. For segments containing artifacts determined by objective methods (e.g., exceeding $\pm200$ $\mu$V in the vertical EOG channel), feedback will not be calculated in order to avoid contamination by blinks or vertical eye movements.

For fNIRS signals, raw signals can be converted to optical density changes by the information receiver 130, and the computation module 140 applies a 0.01-0.5-Hz bandpass filter to remove slow signal drift and high-frequency spikes. The filtered optical density data is then be converted to changes in oxy- and deoxy-haemoglobin concentration by the computation module 140. Then, using the computation module 140, signals from short-separation channels are subtracted from those at long-separation channels to remove the confound of systemic physiology. The computation module 140 calculates the difference between oxy- and deoxy-hemoglobin concentration, generating cerebral oxygenation changes. Similarly to the EEG signals, target objectives are determined by the training modules, including a cognitive module, an affective module, and a social module. For the cognitive module, using the computation module 140, the change in cerebral oxygenation across prefrontal regions can be selected as the target objective, representing frontal activation. For the affective module, using the computation module 140, the difference in the change in cerebral oxygenation between the two hemispheres (left minus right) can be chosen to represent frontal asymmetry. For the social module, using the computation module 140, the change in cerebral oxygenation across sensorimotor regions can be selected as the target objective.

Following baseline correction of the EEG signals by the computation module 140, it can ensure accurate neurofeedback analysis, and then EEG neurofeedback can be acquired with the target objective, including (1) the decrease in frontocentral theta/beta ratio for the cognitive module; (2) the increase in the leftward asymmetry of frontal alpha for the affective module; and (3) mu suppression in sensorimotor regions for the social module. Following baseline correction of the fNIRS signals by the computation module 140, it can ensure accurate neurofeedback analysis, and then fNIRS neurofeedback can be acquired with the target objective, including (1) the increase in bilateral frontal hemodynamic activity for the cognitive module; (2) the increase in the leftward asymmetry of frontal hemodynamic activity for the affective module; and (3) the change in the sensorimotor hemodynamic activity for the social module.

For EEG-fNIRS neurofeedback, the target objective is the minimum of the EEG and fNIRS Z-scores (i.e., a conjunction between the two indices). This can facilitate coupling between the brain's electrical and hemodynamic activity (i.e., neurovascular coupling). Z-score, in one embodiment, is a statistical measure that quantifies how far a particular observation (such as a neurofeedback signal) deviates from the mean of a group of observations; that is the Z-score is calculated based on the baseline data by the computation module 140, which serves as a reference or standard for comparison.

The term "EEG and fNIRS Z-scores" refers to the standardization of the neurofeedback signals obtained from both EEG and fNIRS modalities using the computation module 140. By employing Z-scores, the system normalizes the neurofeedback signals to the baseline, allowing for standardized comparisons within participants. This standardization, facilitated by the computation module 140, is a key component for effectively combining EEG and fNIRS signals. For example, if the EEG neurofeedback signal has a Z-score of +1 unit, and the fNIRS neurofeedback signal has a Z-score of +0.5 units, the computation module 140 will determine the minimum Z-score (i.e., the conjunction) between them as +0.5 units (i.e., the Z-score of +1 unit is determined to be discarded). This combined Z-score represents a unified metric that incorporates information from both EEG and fNIRS. The objective is to facilitate the integration of information about electrical (EEG) and hemodynamic (fNIRS) brain activity. This is why the symbol used inside the blocks in FIG. 3 is the intersection symbol "∩." This operation optimizes computational resources by focusing solely on relevant data for analysis, simplifying operational processes and reducing computer power consumption, and it may speed up the computation for the analysis. That is, it seamlessly integrates EEG and fNIRS modalities while maximizing computational efficiency.

Further, in the present invention, a neurofeedback game operation is provided.

Figure 5:
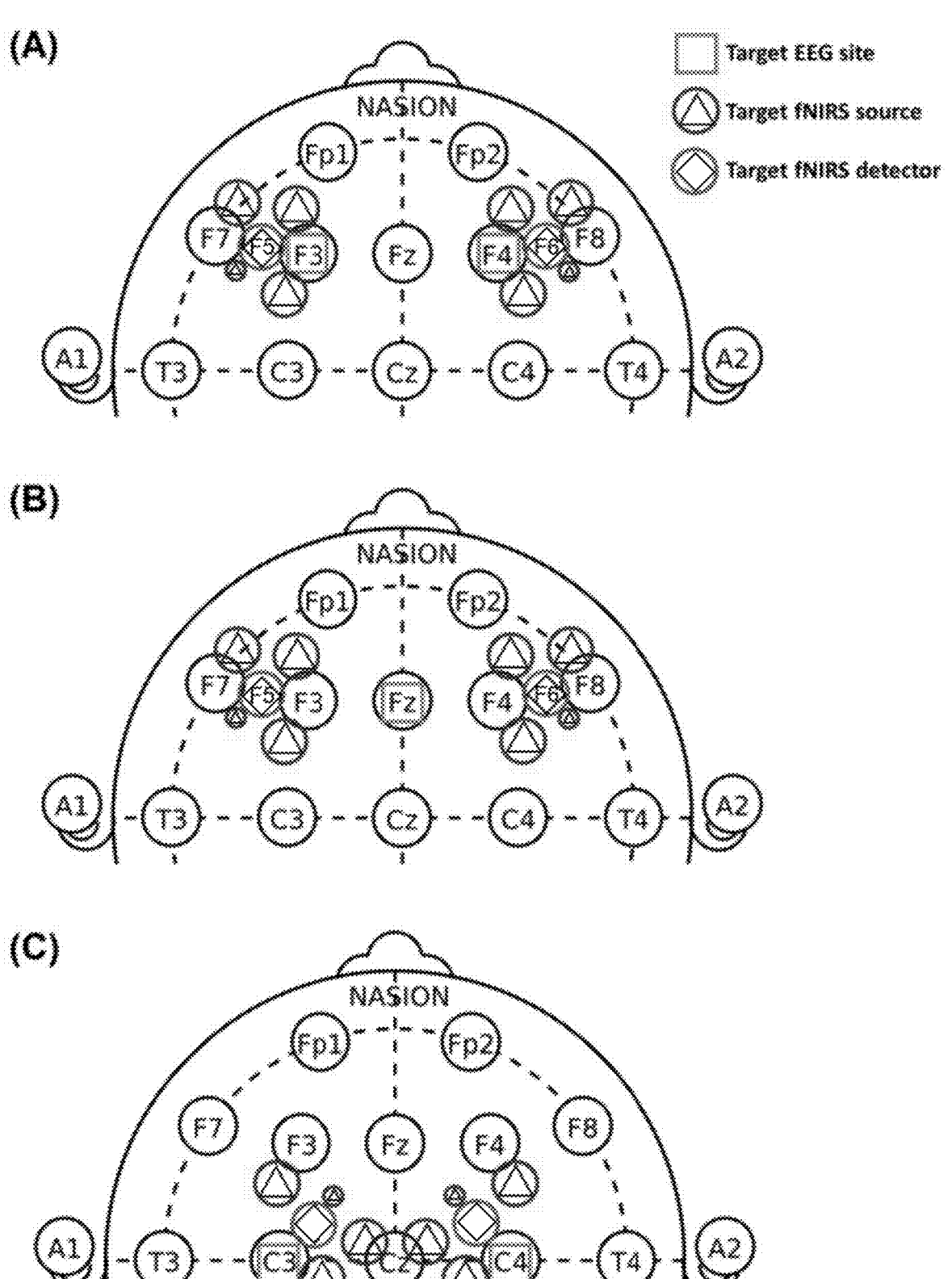
FIG. 5 shows EEG-fNIRS layouts for the different training modules section (A): cognitive module; (B): affective module; and section (C): social module according to one embodiment of the present invention.

After the target index is extracted, it can be used in a neurofeedback training game operation. Details (e.g., expected outcomes and specifications for the neurofeedback game operation) are shown in FIG. 4, which demonstrates training modules offered in the EEG-fNIRS neurofeedback operation; and the EEG-fNIRS layouts for the different training modules (i.e., a cognitive module, an affective module, and a social module) are shown in FIG. 5 with section (A): cognitive module; (B): affective module; and section (C): social module.

At the beginning of each training session, signals are normalized to the mean and standard deviation of all data points over a certain period (e.g., 2 minutes) to establish the baseline. This procedure enables subsequent Z-score training (which is relative to this baseline). Across different modes/modules, points can be rewarded in proportion to how much the target objective is met. The Z-score range are adjusted to vary the difficulty level (default: three levels, including easy, medium, difficult). The higher the upper limit, implying that a stronger modulation of brain activity is needed to gain points, the more difficult the regulation task is. This feature implements progressive overload to ensure that adequate demand is continuously placed on individuals.

The neurofeedback game operation can provide real-time changing game activities with stimuli for participants, which can be achieved through the interactive terminal 106 with the screen. Herein, the "changing game" includes using changing images or video speed to visualize indices, including 6 indices (for the EEG and fNIRS signals) as input to a specifically designed game. For example, changes in images or changes in video speed are displayed for participants via the screen of the interactive terminal 106.

During training within the game, participants engage with the interactive terminal 106, looking at its screen to interact with an intrinsically rewarding stimulus in real time. The stimulus dynamically changes based on the degree to which the target objective is met, represented by the Z-score. In this context, the computation module 140, which is connected or coupled with the interactive terminal 106, can transmit score information to the interactive terminal 106. The interactive terminal 106 then determines and displays the stimulus changes on its screen for the participants according to the score information. This integrated feedback loop ensures that participants receive immediate visual or auditory feedback reflecting their performance and adherence to the training objectives.

For the cognitive module, individuals can watch a video clip with contents preferred by autistic children, such as animated geometric patterns. The playback speed can be determined by the Z-score. For the affective module, the stimulus can be an avatar or human face morphed between a neutral and a happy face, and the degree of happiness can vary according to the Z-score. For the social module, individuals see a video of hand and finger movements, along with a left- or right-pointing arrow. The hand moves horizontally in accordance with the pointing direction of the arrow, and the horizontal distance of the hand from the screen center represents the Z-score.

The interactive mode is facilitated through the collaboration between the computation module 140 and the interactive terminal 106. Specifically, the computation module 140 calculates the Z-scores based on EEG and fNIRS signals, interpreting the neural feedback data. Subsequently, this score information is transmitted to the interactive terminal 106, where the screen display is dynamically adjusted and updated according to the Z-scores. For instance, on the screen of the interactive terminal 106, the playback speed, facial expressions, and hand movement patterns are modified in real time, ensuring that the neurofeedback training is tailored to each individual's cognitive, affective, and social needs.

Furthermore, there are three default difficulty levels, determined by three Z-score ranges (easy: 0 to 0.5; medium: 0 to 1.0; difficult: 0 to 1.5). Individuals can gain one point for reaching every 10% of the Z-score range. Points are updated every second, and the total points are shown on the screen. A maximum of 3,000 points can be gained in 5 minutes (10 points×300 seconds). Participants can proceed to the next difficulty level when securing more than 2000 points for two rounds in a row. However, they will return to the previous level when obtaining fewer than 1,000 points in two consecutive rounds.

In collaboration with the interactive terminal 106 and the computation module 140, the EEG-fNIRS neurofeedback results can be input into the report generator 150, providing users with a comprehensive overview of their neurofeedback training (e.g., a physical report). The report generator 150 is designed to meticulously document the Z-score selection process during neurofeedback sessions. Specifically, when determining the minimum Z-score between the EEG and fNIRS indices, the report generator 150 not only records the selected minimum Z-score but also lists the alternative value that is discarded. In one embodiment, if the discarded Z-score significantly deviates from the selected minimum Z-score, the report generator 150 can additionally be configured to issue an alert within the report. This alert serves to notify users of potential variability in the neurofeedback signals, enhancing their awareness and understanding of the training outcomes.

As above, the EEG-fNIRS neurofeedback system of the present invention is designed to address limitations in existing products while facilitating optimized and widespread neurofeedback training. Comparisons between the EG-fNIRS neurofeedback system of the present invention and the existing prior art are provided in Table 2 of FIG. 6. In this regard, the neurofeedback systems implemented in these prior-art products lack at least one of the following essential elements: (1) the use of relatively established EEG neurofeedback training protocols; (2) the adoption of ecologically valid and intrinsically reward training and feedback stimuli to stimulate motivation; (3) the implementation of a personalized program implemented with progressive overload to continuously place adequate demand for continual improvement; (4) a cross-device application that allows for widespread use; or (5) software and hardware support for high-quality neurofeedback training via implementation of effective artifact rejection and correction algorithms.

The functional units and modules of the systems for recognizing participating activities and computing a subject's attention level in accordance with the embodiments disclosed herein may be implemented using computing devices, computer processors, or electronic circuitries including but not limited to application specific integrated circuits (ASIC), field programmable gate arrays (FPGA), microcontrollers, and other programmable logic devices configured or programmed according to the teachings of the present disclosure. Computer instructions or software codes running in the computing devices, computer processors, or programmable logic devices can readily be prepared by practitioners skilled in the software or electronic art based on the teachings of the present disclosure.

All or portions of the methods in accordance to the embodiments may be executed in one or more computing devices including server computers, personal computers, laptop computers, mobile computing devices such as smartphones and tablet computers.

The embodiments may include computer storage media, transient and non-transient memory devices having computer instructions or software codes stored therein, which can be used to program or configure the computing devices, computer processors, or electronic circuitries to perform any of the processes of the present invention. The storage media, transient and non-transient memory devices can include, but are not limited to, floppy disks, optical discs, Blu-ray Disc, DVD, CD-ROMs, and magneto-optical disks, ROMs, RAMs, flash memory devices, or any type of media or devices suitable for storing instructions, codes, and/or data.

Each of the functional units and modules in accordance with various embodiments also may be implemented in distributed computing environments and/or Cloud computing environments, wherein the whole or portions of machine instructions are executed in distributed fashion by one or more processing devices interconnected by a communication network, such as an intranet, Wide Area Network (WAN), Local Area Network (LAN), the Internet, and other forms of data transmission medium.

The foregoing description of the present invention has been provided for the purposes of illustration and description. It is not intended to be exhaustive or to limit the invention to the precise forms disclosed. Many modifications and variations will be apparent to the practitioner skilled in the art.

The embodiments were chosen and described in order to best explain the principles of the invention and its practical application, thereby enabling others skilled in the art to understand the invention for various embodiments and with various modifications that are suited to the particular use contemplated.

What is claimed is:

1. An integrated electroencephalogram-functional near-infrared spectroscopy (EEG-fNIRS) neurofeedback system for reducing power consumption, the EEG-fNIRS neurofeedback system being for interacting with participant's brain activity and comprising:

EEG electrodes configured to collect EEG signals;

fNIRS detectors configured to collect fNIRS signals;

at least one information receiver electrically coupled with the EEG electrodes and the fNIRS detectors and configured to receive and process the collected EEG and fNIRS signals from the EEG electrodes and the fNIRS detectors, respectively;

a computation module electrically coupled with the information receiver and configured to execute an EEG and fNIRS signal processing pipeline with the EEG electrodes, the fNIRS detectors, and the information receiver, wherein the computation module is further configured to:

calculate score information based on received EEG and fNIRS signals, comprising standardizing neurofeedback signals obtained from both of the EEG and fNIRS signals so as to obtain a first Z-score for EEG neurofeedback and a second Z-score for fNIRS neurofeedback, thereby normalizing the EEG and fNIRS signals to baseline and allowing for standardized comparisons within the participant, wherein a combination of the first Z-score and the second Z-score represents a unified metric that incorporates information from both of the EEG and fNIRS signals to facilitate an integration of information about electrical and hemodynamic brain activity;

select a minimum score from the calculated score information of the first Z-score and the second Z-score for serving as a common target objective shared by both EEG and fNIRS signals, wherein both the EEG and fNIRS signals are processed in real time; and discard an alternative score of the first Z-score and the second Z-score that is not selected as the minimum score, so as to enable the computation module to choose a single representative score for the shared target objective from both EEG and fNIRS signals, thereby focusing solely on relevant data for analysis;

a report generator electrically coupled with the computation module and configured to provide a report of the selection to the minimum score; and an interactive terminal with a screen electrically coupled with the computation module and configured to display images or videos via the screen thereof, enabling real-time interaction with an intrinsically rewarding stimulus for at least one participant, wherein the interactive terminal is further configured to display a video clip with animated geometric patterns via the screen thereof, and wherein the interactive terminal is further configured to display a video of hand and finger movements via the screen thereof and to determine and adjust a horizontal distance of the hand from the center of a screen according to the selected minimum score provided by the computation module.

2. The integrated EEG-fNIRS neurofeedback system of claim 1, wherein the interactive terminal is further configured to determine and adjust a playback speed for the video clip according to the selected minimum score provided by the computation module.

3. The integrated EEG-fNIRS neurofeedback system of claim 1, wherein the interactive terminal is further configured to display an avatar or human face via the screen thereof.

4. The integrated EEG-fNIRS neurofeedback system of claim 1, wherein display in the screen of the interactive terminal is dynamically adjusted and updated according to the selected minimum score provided by the computation module.

5. The integrated EEG-fNIRS neurofeedback system of claim 1, wherein the report generator is further configured to record the selected minimum score provided by the computation module as well as list the alternative score that is discarded.

6. The integrated EEG-fNIRS neurofeedback system of claim 5, wherein the report generator is further configured to issue an alert within the report if the discarded alternative score significantly deviates from the selected minimum score.

7. An integrated electroencephalogram-functional near-infrared spectroscopy (EEG-fNIRS) neurofeedback method for reducing power consumption, the EEG-fNIRS neurofeedback method being for interacting with participant's brain activity and comprising:

collecting EEG signals by EEG electrodes;

collecting fNIRS signals by fNIRS detectors;

receiving and processing, by at least one information receiver, the collected EEG and fNIRS signals from the EEG electrodes and the fNIRS detectors, respectively;

executing an EEG and fNIRS signal processing pipeline by using the EEG electrodes, the fNIRS detectors, the information receiver, and a computation module;

calculating score information based on received EEG and fNIRS signals by the computation module, comprising standardizing neurofeedback signals obtained from both of the EEG and fNIRS signals so as to obtain a first Z-score for EEG neurofeedback and a second Z-score for fNIRS neurofeedback, thereby normalizing the EEG and fNIRS signals to baseline and allowing for standardized comparisons within the participant, wherein a combination of the first Z-score and the second Z-score represents a unified metric that incorporates information from both of the EEG and fNIRS signals to facilitate an integration of information about electrical and hemodynamic brain activity;

selecting, by the computation module, a minimum score from the calculated score information of the first Z-score and the second Z-score for serving as a common target objective shared by both EEG and fNIRS signals, wherein both the EEG and fNIRS signals are processed in real time;

discarding, by the computation module, an alternative score of the first Z-score and the second Z-score that is not selected as the minimum score, so as to choose a single representative score for the shared target objective from both EEG and fNIRS signals, thereby focusing solely on relevant data for analysis;

providing a report of the selection to the minimum score by a report generator;

displaying images or videos by an interactive terminal with a screen, so as to enable real-time interaction with an intrinsically rewarding stimulus for at least one participant;

displaying a video clip with animated geometric patterns via the screen;

displaying a video of hand and finger movements via the screen; and determining and adjusting a horizontal distance of the hand from the center of a screen according to the selected minimum score.

8. The integrated EEG-fNIRS neurofeedback method of claim 7, further comprising determining and adjusting a playback speed for the video clip according to the selected minimum score provided by the computation module.

9. The integrated EEG-fNIRS neurofeedback method of claim 7, further comprising displaying an avatar or human face via the screen.

10. The integrated EEG-fNIRS neurofeedback method of claim 7, wherein display in the screen of the interactive terminal is dynamically adjusted and updated according to the selected minimum score provided by the computation module.

11. The integrated EEG-fNIRS neurofeedback method of claim 7, further comprising recording the selected minimum score provided by the computation module as well as listing the alternative score that is discarded.

12. The integrated EEG-fNIRS neurofeedback method of claim 11, further comprising issuing an alert within the report if the discarded alternative score significantly deviates from the selected minimum score.

\* \* \* \* \*